(12) United States Patent
Koptenko et al.

(10) Patent No.: US 11,925,510 B2
(45) Date of Patent: Mar. 12, 2024

(54) DIAGNOSTIC ULTRASOUND MONITORING SYSTEM AND METHOD

(71) Applicant: URSUS Medical Designs LLC, Pittsburgh, PA (US)

(72) Inventors: Sergei Koptenko, Mississauga (CA); Thomas Hayes, Allison Park, PA (US); Matthew Lyon, North Augusta, SC (US)

(73) Assignee: URSUS MEDICAL DESIGNS LLC, Pittsburgh, PA (US)

(*) Notice: Subject to any disclaimer, the term of this patent is extended or adjusted under 35 U.S.C. 154(b) by 0 days.

(21) Appl. No.: 17/973,386

(22) Filed: Oct. 25, 2022

(65) Prior Publication Data
US 2023/0093482 A1 Mar. 23, 2023

Related U.S. Application Data

(63) Continuation of application No. 16/348,968, filed as application No. PCT/US2017/061409 on Nov. 13, 2017, now Pat. No. 11,478,227.
(Continued)

(51) Int. Cl.
*A61B 8/06* (2006.01)
*A61B 8/00* (2006.01)
(Continued)

(52) U.S. Cl.
CPC .............. *A61B 8/56* (2013.01); *A61B 8/06* (2013.01); *A61B 8/4427* (2013.01);
(Continued)

(58) Field of Classification Search
CPC ...... A61B 2017/00106; A61B 2505/01; A61B 2562/046; A61B 5/0024; A61B 5/01; A61B 5/026; A61B 5/14551; A61B 8/06; A61B 8/0883; A61B 8/4227; A61B 8/4245; A61B 8/4281; A61B 8/4416; A61B 8/4427; A61B 8/4472; A61B 8/4477; A61B 8/4488; A61B 8/461; A61B 8/462; A61B 8/485;
(Continued)

(56) References Cited

U.S. PATENT DOCUMENTS 6,390,996 B1 5/2002 Halperin et al.
6,705,992 B2 3/2004 Gatzke
(Continued)

FOREIGN PATENT DOCUMENTS

WO 2011001346 6/2011

*Primary Examiner* — Jon Eric C Morales
(74) *Attorney, Agent, or Firm* — Blynn L. Shideler; Krisanne Shideler; BLK Law Group

(57) ABSTRACT

A distributed patient monitoring system comprises at least one standalone portable ultrasound imaging unit configured to be fixed to a stable position against the skin on a patient's body and capable of prolonged ultrasound data acquisition, including an ultrasound imaging array, transmit-receive circuitry, a beamformer, backend signal and image processing subsystem, power and communication subsystems, and a monitoring workstation connected to each standalone portable ultrasound imaging unit configured to request and receive ultrasound imaging information from each standalone portable ultrasound imaging unit, and configured to analyze and display acquired ultrasound information.

6 Claims, 4 Drawing Sheets

Related U.S. Application Data

(60) Provisional application No. 62/420,677, filed on Nov. 11, 2016.

(51) Int. Cl.
*A61B 8/08* (2006.01)
*A61H 31/00* (2006.01)
*A61N 5/10* (2006.01)
*A61B 17/00* (2006.01)

(52) U.S. Cl.
CPC .......... *A61B 8/4472* (2013.01); *A61B 8/4477* (2013.01); *A61B 8/4488* (2013.01); *A61B 8/462* (2013.01); *A61B 8/485* (2013.01); *A61B 8/488* (2013.01); *A61B 8/5246* (2013.01); *A61H 31/005* (2013.01); *A61N 5/1049* (2013.01); *A61B 8/4227* (2013.01); *A61B 8/4281* (2013.01); *A61B 2017/00106* (2013.01); *A61N 2005/1058* (2013.01)

(58) Field of Classification Search
CPC ......... A61B 8/488; A61B 8/5246; A61B 8/56; A61N 1/3993; A61N 2005/1058; A61N 5/1049; G06T 2207/30196; G06T 7/0012; A61H 2201/5058; A61H 2201/5043; A61H 2201/5097; A61H 2230/255; A61H 2201/0157; A61H 31/005

See application file for complete search history.

(56) References Cited

U.S. PATENT DOCUMENTS

| | | | |
|---|---|---|---|
| 7,074,199 | B2 | 7/2006 | Halperin et al. |
| 8,600,522 | B2 | 12/2013 | Peterson et al. |
| 8,622,913 | B2 | 1/2014 | Dentinger et al. |
| 2009/0043199 | A1 | 2/2009 | Pelissier et al. |
| 2009/0043203 | A1 | 2/2009 | Pelissier et al. |
| 2009/0043204 | A1 | 2/2009 | Pelissier et al. |
| 2009/0198132 | A1 | 8/2009 | Pelissier et al. |
| 2009/0306525 | A1 | 12/2009 | Pinter et al. |
| 2011/0034836 | A1 | 2/2011 | Halperin et al. |
| 2014/0163436 | A1 | 6/2014 | Peterson et al. |
| 2014/0187975 | A1 | 7/2014 | Halperin et al. |
| 2014/0342331 | A1* | 11/2014 | Freeman ............. H04N 23/698 434/265 |
| 2020/0187916 | A1 | 6/2020 | Koptenko |

* cited by examiner

DIAGNOSTIC ULTRASOUND MONITORING SYSTEM AND METHOD

RELATED APPLICATIONS

The present application claims is a continuation of U.S. patent application Ser. No. 16/348,968 that was the national stage of International Application PCT/US2017/061409.

U.S. patent application Ser. No. 16/348,968 published Jun. 18, 2020 as Publication number 2020-018916 and issued Oct. 25, 2022 as U.S. Pat. No. 11,478,227. International Application PCT/US2017/061409 published May 17, 2018 as Publication WO2018-089949. The above identified publications and patent are incorporated herein by reference.

International Application PCT/US2017/061409 claims priority to U.S. Provisional Patent Application Ser. No. 62/420,677 titled "Diagnostic Ultrasound Monitoring System and Method" and filed Nov. 11, 2016 which is incorporated herein by reference.

BACKGROUND INFORMATION

1. Field of the Invention

The present invention relates to ultrasonic diagnostic imaging. More specifically, the present invention relates to diagnostic and health monitoring applications in the field of medical ultrasonography.

2. Background of the Invention

Ultrasound imaging is a universally accepted diagnostic modality used in a range of medical applications. Present-day diagnostic ultrasound imaging systems, as a rule, operate in clinical setting as stand-alone instruments providing static intermittent 2D or 3D snapshots or short video loops of the patient's organ or locality. While this mode of operation meets the great majority of diagnostic needs, there are significant number of clinical tasks that require more than just a short time observation of a region of interest (ROI) in the patient's body.

The want for a long term observation of an organ or a Region of Interest (ROI) could rise from a need to monitor the healing progress in trauma or surgery site, detect blood clot appearance in blood vessels, heart monitoring to predict the cardiac collapse (e.g., hemorrhagic or hypovolemic shock, septic shock, etc.) in trauma patients, heart or organ monitoring during surgery or treatment, or to provide a rescuer with information relating to the efficacy of chest compressions, return of spontaneous circulation, and underlying cardiac rhythm without cessation of external cardiac compression (CPR) and many other clinical situations. Another important application of remotely controlled scanning device is in telemedicine, which adds a whole variety diagnostic tasks to the list of potential applications.

Ultrasound systems known in the art are ill suited for any above mentioned tasks since they rely on manual positioning and manipulation of the probe, requiring a constant presence of a trained, experienced sonographer, that essentially preclude any long term observations or receiving a long term data input from a stable monitoring position. Comparing periodic examinations of the same organ is also met with difficulty, since it is extremely hard to replicate the previous scanning conditions (probe position, orientation, etc.) exactly. Thus, a small portable wireless ultrasound unit that can be strapped or in some other way fixed to the stable position against the skin on a patient's body and capable of prolonged data acquisition would offer significant advantages in patient care.

Prior art for such ultrasound patient monitoring systems includes general use devices, as well as, devices designed for performing some specific clinical tasks. U.S. Pat. Application Publications US20090043199A1 and US20090043199A1 titled "Wireless network having portable ultrasound devices", and which are incorporated herein by reference, each disclose a patient monitoring system comprising of a wireless ultrasound device and a display station connected via network to receive and display ultrasound data from the ultrasound device. The system is capable of detecting a heartbeat signal and produce an alarm signal if patient's heart beat deviate from the preset range of values.

Philip's U.S. Pat. No. 6,705,992 titled "Ultrasound imaging enhancement to clinical patient monitoring functions", which is incorporated herein by reference, discloses a patient monitoring system continuously generating ultrasound images (such as transesophageal echocardiogram (TEE)) from a patient and continuously analyze the data to extract physiological diagnostic data corresponding to adjunct physiological functions of the patient monitoring information and to generate ultrasound based trend analysis data of the physiological functions, wherein the algorithms include at least one of an automatic boundary extraction algorithm, regional wall motion algorithm, an automatic gain control algorithm, kinesis measurement, and a physiological measurement.

General Electric Company's U.S. Pat. No. 8,622,913 titled "Method and system for non-invasive monitoring of patient parameters" which is incorporated herein by reference, discloses a method for continuous non-invasive monitoring of multiple arterial parameters of a patient.

One significant area for potential applications of portable ultrasound monitors is the cardiopulmonary resuscitation procedures (CPR) with the main goal of the portable ultrasound monitor being to provide a rescuer with information relating to the efficacy of chest compressions, return of spontaneous circulation, and underlying cardiac rhythm without cessation of external cardiac compression during CPR. Philip's Pat. Application Publication No. US2009/0306525 titled "Apparatus and method for defibrillation with pulse detection using electromagnetic waves" discloses a pulse detector that uses electromagnetic waves for detecting a patient pulse in conjunction with the administration of defibrillation and/or CPR.

There are numerous patents describing proposed CPR feedback systems and methods. U.S. Pat. Application Publication No. 2014/0163436 titled "CPR feedback method and apparatus", U.S. Pat. No. 8,600,522 titled "CPR feedback method and apparatus", WO 2011001346 titled "A cardiopulmonary resuscitation (CPR) feedback system", U.S. Pat. No. 6,390,996 titled "CPR chest compression monitor", U.S. Pat. No. 7,074,199 titled "CPR chest compression monitor and method of use", U.S. Patent Application Publication No. 2014/0187975 titled "ECG Artifact Reduction System", U.S. Patent Application Publication No. 2011/0034836 titled "Wrist Mounted CPR Chest Compression Monitor", which patents and publications are collectively incorporated herein by reference, all address the need for feedback during the CPR, however none of the listed patents or published applications incorporate the measurements of cerebral blood flow as a true outcome measure and therefore do not optimize CPR according to blood flow and account for respirations, changes in chest compliance, air trapping due to rapid ventilation, etc.

There remains a need in the art for an ultrasound monitoring system and associated method and components for use in monitoring physiological conditions and parameters accurately and without requiring frequent intervention of a trained operator. There is further a need for a portable ultrasound monitor system configured for use with existing cardiopulmonary resuscitation procedures (CPR) with the portable ultrasound monitor being configured to provide a rescuer with information relating to the efficacy of chest compressions, return of spontaneous circulation, and underlying cardiac rhythm all without cessation of external cardiac compression during CPR.

BRIEF SUMMARY OF THE INVENTION

The task of long-term remote ultrasound monitoring, among other things, requires solving the problem of miniaturization of the diagnostic ultrasound system, scaling weight, power consumption and geometrical dimensions down to the smartphone form factor level and minimization of operator's involvement into the monitoring process, preferably limited to the initial placement and securing the device on the selected location on patient's body.

In an exemplary embodiment, the present invention comprises of a portable standalone ultrasound imaging unit, and a remote patient monitoring system. A portable ultrasound imaging unit works by intermittently or continuously generating ultrasound images and possibly some physiology signals from a patient, continuously analyzing and extracting the diagnostic data and transmitting said data and images to the remote patient monitoring system via wired or wireless data transmission link directly or via interface unit. A remote patient monitoring system may comprise of a portable display unit, a display station, a remote workstation, a cloud-based data storage and analysis hardware and software, a telemedicine workstation hardware and software, and communication channels software and hardware to transmit data between the portable ultrasound imaging unit and a remote patient monitoring system. The monitoring system may also utilize an integrated visual display to provide real-time analysis of the patient's physiology or condition.

One application of the present invention provides a portable ultrasound monitor system configured for use with existing cardiopulmonary resuscitation procedures (CPR) with the portable ultrasound monitor being configured to provide a rescuer with information relating to the efficacy of chest compressions, return of spontaneous circulation, and underlying cardiac rhythm all without cessation of external cardiac compression during CPR.

One aspect of the present invention provides a distributed patient monitoring system comprising at least one standalone portable ultrasound imaging unit configured to be fixed to a stable position against the skin on a patient's body and capable of prolonged ultrasound data acquisition, including an ultrasound imaging array, transmit-receive circuitry, a beamformer, backend signal and image processing subsystem, power and communication subsystems, and a monitoring workstation connected to each standalone portable ultrasound imaging unit configured to request and receive ultrasound imaging information from each standalone portable ultrasound imaging unit, and configured to analyze and display acquired ultrasound information.

The distributed patient monitoring system according to one aspect of the invention provides wherein a plurality of standalone portable ultrasound imaging units are connected to a single patient to monitor conditions of the patient from different scanning positions and orientations.

The distributed patient monitoring system according to one aspect of the invention provides wherein a plurality of standalone portable ultrasound imaging units are connected to a multitude of patients to monitor the patients' conditions The distributed patient monitoring system according to one aspect of the invention provides wherein the monitoring workstation is configured to request ultrasound image from each standalone portable ultrasound imaging unit intermittently or continuously, and wherein an imaging frame orientation, a frequency of acquisition, and scanning parameters requested are pre-programed.

The distributed patient monitoring system according to one aspect of the invention provides wherein an imaging frame orientation, a frequency of acquisition, and scanning parameters, are set dynamically by the monitoring workstation for each standalone portable ultrasound imaging unit in accordance to the patient's condition.

The distributed patient monitoring system according to one aspect of the invention provides wherein an imaging frame orientation, a frequency of acquisition, and scanning parameters for each standalone portable ultrasound imaging unit are controlled from a remote location.

The distributed patient monitoring system according to one aspect of the invention provides wherein the monitoring workstation is configured to display at least one integrated parameter related to patient health condition inferred from ultrasound image and from ancillary sensor data. The distributed patient monitoring system may further provide wherein a monitoring workstation is configured to alert operator to changes in at least one integrated parameter related to patient health condition inferred from ultrasound image and ancillary sensor data that indicates a worsening patient condition or an equipment malfunction. The distributed patient monitoring system according to the present invention may provide wherein the monitoring workstation is configured to alert operator to changes in at least one integrated parameter related to patient health condition and configured to suggest the operator an optimal course of action.

The distributed patient monitoring system according to one aspect of the invention provides wherein the monitoring workstation is configured to wirelessly transmit patient data to an ancillary portable display.

The distributed patient monitoring system according to one aspect of the invention provides wherein each ultrasound imaging array comprises a 2D array. The distributed patient monitoring system according to invention may provide wherein each 2D ultrasound imaging array, transmit-receive circuitry, and beamformer are formed as a single chip ultrasound system. The distributed patient monitoring system according to the invention may provide wherein each standalone portable ultrasound imaging unit comprises the single chip ultrasound system, battery and wireless communication sub-system The distributed patient monitoring system according to one aspect of the invention provides wherein each standalone portable ultrasound imaging unit includes a small visual display attached to unit and configured to display at least one of i) vital integrated data or health parameters the unit receives from the workstation, ii) progress of the scan, iii) guidance and directions to the operator for the attention of the operator or a patient.

The distributed patient monitoring system according to one aspect of the invention provides wherein ultrasound data recorded by each unit comprises at least one of raw RF data, I/Q data, B-mode data, continuous wave Doppler, color Doppler, vector flow imaging data, shear-wave elastography (SWE), and acoustic radiation pressure imaging data.

The distributed patient monitoring system according to one aspect of the invention provides wherein at least one standalone portable ultrasound imaging unit is configured to measure the carotid blood flow for detecting the underlying rhythm during cardiopulmonary resuscitation (CPR) in order to provide the rescuer with information relating to the efficacy of chest compressions, return of spontaneous circulation, and/or underlying cardiac rhythm without cessation of external cardiac compression.

The distributed patient monitoring system according to one aspect of the invention provides wherein a plurality of standalone portable ultrasound imaging units are provided and configured to obtain a combined fused image or data volume from separate image or data volumes produced by each unit.

The distributed patient monitoring system according to one aspect of the invention provides wherein at least one standalone portable ultrasound imaging unit is equipped with position and orientation sensors.

The distributed patient monitoring system according to one aspect of the invention provides wherein at least standalone portable ultrasound imaging unit is configured to obtain an image or data volume from a static location while at least one standalone portable ultrasound imaging unit is configured for free hand image acquisition.

The distributed patient monitoring system according to one aspect of the invention provides wherein at least one standalone portable ultrasound imaging unit is configured to aid in organ position tracking during an image guided radiation treatment, surgery or for long term organ monitoring.

The distributed patient monitoring system according to one aspect of the invention provides wherein an autonomous portable ultrasound imaging device allows remotely guided or automatic image position optimization and scanning parameter optimization These and other advantages of the present invention will be clarified in the brief description of the preferred embodiment taken together with the drawings in which like reference numerals represent like elements throughout.

These together with other objects and advantages, which will be subsequently apparent, reside in the details of construction and operation as more fully hereinafter described and claimed, reference being had to the accompanying drawings forming a part hereof, wherein like numerals refer to like parts throughout.

DETAILED DESCRIPTION OF THE INVENTION

The present invention relates to ultrasound diagnostic systems, such as used in medical diagnostic systems for medical human and animal applications. Some aspects of the present invention, such as the construction and operation of an analog store digital read beamforming system and method are understood in connection with WO/2014/125371, corresponding to PCT/IB2014/000281 and WO/2016/077822 corresponding to PCT/US15/60861, which applications are incorporated herein by reference. The analog store digital read beamforming system and method used in the present system allows for each channel to use less than 40 milliwatts in operation and generally less than 25 milliwatts in operation. Outside of human and animal applications, the system and method of the present invention is also applicable to non-destructive testing/evaluation (e.g., pipeline testing, airframe testing, turbine blades testing, bridge and structural testing, and manufacturing testing), particularly where there is a need for task of long-term remote ultrasound monitoring. The system and method of the present invention is also applicable to sonar applications, and generally any ultrasound imaging (or image-like) applications requiring long term ultrasound based monitoring.

The present invention is directed in particular the way signals coming from the one, or a bank or series, of compact standalone ultrasound imaging units are treated. The invention describes an improved ultrasound monitoring system that provides better image quality combined with significant reduction in systems' size, power consumption and production cost as compared to current systems.

Thus, even though the main area of application of this invention is in medical ultrasound, this architecture and the hardware and software built upon its principles can be used in other areas such as non-destructive testing, sonar, radar, terahertz, infrared, optical imaging systems or for seismic geophysical exploration, just to name a few examples.

The general idea of the invention is to create a remote patient monitoring system that would use a portable stand-alone ultrasound imaging unit, and optionally physiological signals from an ancillary array of sensors, to remotely monitor the patient's health, diagnose the patient condition and alert an operator if some actions need to be taken.

Figure 1:
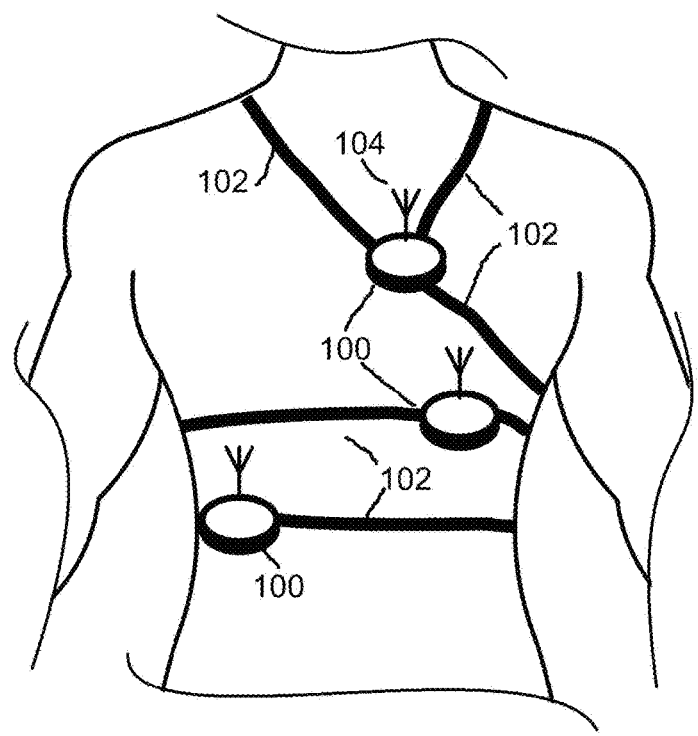
FIG. 1 illustrates a possible arrangement of portable ultrasound imaging units of a diagnostic ultrasound monitoring system according to one embodiment of the present invention with the units attached to regions of interest of the patient and secured by an elastic strap system.
Figure 2B:
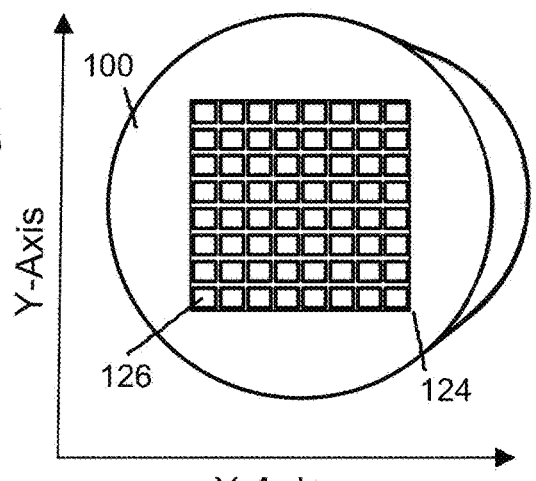
FIG. 2B is a schematic illustration of a 2D ultrasound array in a portable ultrasound imaging unit of a diagnostic ultrasound monitoring system according to one embodiment of the present invention.

FIGS. 1-3 illustrates a remote patient monitoring system formed in accordance with an embodiment of the present invention. As FIG. 1 illustrate, portable standalone ultrasound imaging units 100 can be securely attached to the skin by a probe mounts (elastic bands) 102. The units 100 are described as standalone, or autonomous or hands-free because they do not require a technician to hold the unit 100 in position to operate and can operate over a long operational sequence as described herein.

Specialized mounting components may be provided for stable positioning on different places of a subject's anatomy and are designed with one or more integral or detachable mounts for receiving a portable ultrasound unit 100, and positioning such a unit 100 on a skin surface of a patient. Elastic bands, skin adhesive or similar components may be provided to at least partially underlie the framework component of the unit 100, providing a comfortable interface with a subject's anatomical surface and providing an effective mounting surface for a framework component. In one embodiment, a band 102 may be provided as a flexible, elastic component sized and configured to contact (directly or indirectly) a desired location on a subject's anatomy and provide a contact surface for a framework component of the unit 100.

In some embodiments, bands 102 provided for contacting a subject are adjustable and may incorporate padding or comprise a material that's comfortable against a skin surface.

In some embodiments, bands 102 provided for contacting a subject and providing an interface for positioning the framework component of each unit 100 may comprise both flexible and substantially rigid portions.

In some embodiments, such bands 102 may be provided with stiff framework interface member(s) that mate with a corresponding interface member(s) provided on the framework component of each unit 100 for stably and positively positioning the framework component of the unit 100 on the band. In some embodiments, the imaging unit 100 may be temporarily or semi-permanently attached to the skin of the patient using skin adhesive.

The probe mount system also allows for an ultrasonically transparent standoff pad (spacer) be secured between the unit 100 and the patient's skin for imaging of hard to reach places, or for other reasons.

Figure 2A:
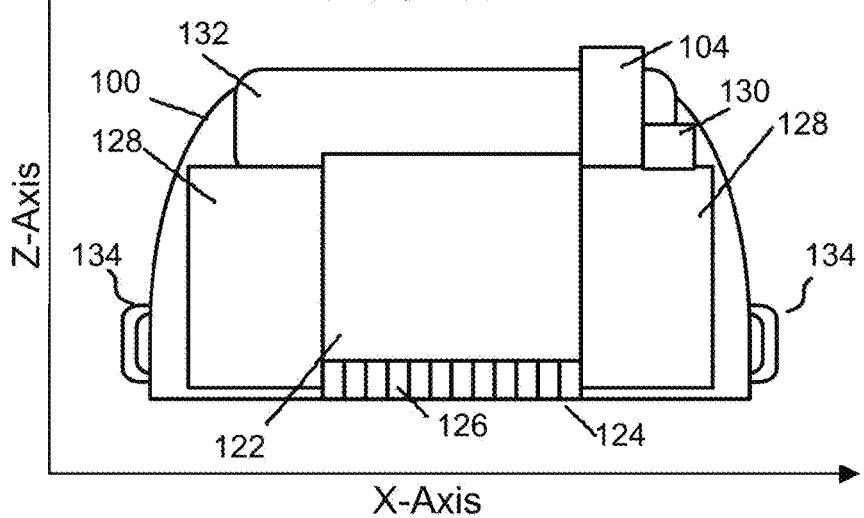
FIG. 2A is a schematic illustration of a possible arrangement of functional blocks in a portable ultrasound imaging unit of a diagnostic ultrasound monitoring system according to one embodiment of the present invention.

Each portable ultrasound imaging unit 100 is a small, generally a disc which is 25 mm in height and 75 mm in diameter or smaller, standalone battery powered, analog store digital read, ultrasound device that wirelessly transmits ultrasound data or images via wireless link 104, or wired link 106, to a remote patient monitoring system, workstation or a display. FIG. 2A shows a schematic outline of device cross-section to schematically illustrate the most important components of such a portable ultrasound imaging unit 100.

The preferred embodiment has the ultrasound 2D array 124 with fully addressable elements 126, however in other embodiment this array 124 can be an annular, curved, linear or some combination thereof, of a phased 1.75D, 1.5D, or 1D array, composed of piezo, cMUT or pMUT elements.

The array is connected to analog front-end and beamformer 122 that outputs analog beamformed RF signal to the back-end block 128 where this signal is digitized and processed to for an ultrasound image frame.

In other embodiments, the array 124 is divided into a number of sub-apertures and analog front-end 122 instead of a single RF signal is capable of producing a multitude of beamformed analog RF signal one for every sub-aperture.

In other embodiments, the portable ultrasound imaging unit may have a visual display attached to the top or being an integral part of the device itself, that may be used to display some vital integrated data, such as a progress of the scan, guidance and directions to the operator or other information for immediate attention of the operator or a patient.

In the preferred embodiment, ultrasound unit 100 is capable of continuously acquiring ultrasound data or can be program to acquire a frame or volume of data intermittently In the preferred embodiment, the 2D array 124 of ultrasound unit 100 is fully addressable such that remote operator can select which plane or a volumetric slice to capture.

In the preferred embodiment, ultrasound unit 100 is capable of continuously or intermittently acquiring ultrasound data for B-mode imaging as well as for various other ultrasound modalities including, but not limited to, continuous wave Doppler, color Doppler, vector flow imaging methods, shear-wave elastography (SWE), acoustic radiation pressure imaging etc.

In one embodiment, a portable ultrasound unit can be a TEE probe with wireless link to the workstation 110.

In another embodiment one or some of ultrasound units 100 could be connected to other medical devices, such as a nasogastric tube, endotracheal tube, Foley catheter, etc.

In another embodiment one or some of ultrasound units 100 could be placed within a body cavity, such as rectal or gynecological probes for IGRT organ position tracking, surgery or monitoring.

The digitized data from the back-end processor 128 are sent to the remote workstation 110 via wireless data controller 130. In the preferred embodiment controller 130 is capable of operating in WiFi mode or UWB or Bluetooth mode depending on the data throughput, range and power available.

In another embodiment, wireless controller 130 is also capable of sending data via wired link using available common data transfer protocol such as USB3.

Each portable ultrasound unit 100 can work for extended periods of time ether on batteries 132 or using external power.

The portable ultrasound unit 100 also has brackets 134 for straps or mounts that keep the unit 100 secured on the patient's body.

In one embodiment, the portable ultrasound unit has additional array of sensors 140 that can provide supplemental physiological data, such as skin temperature, conductivity, pulse, blood oxygenation levels (such as via photoplethysmography), etc. to the monitoring station 110. The types of supplemental physiologic sensors 140 is limitless and any known sensors with low power requirements can be utilized as desired. In another embodiment, some of additional sensors 140 could be interventional.

In one embodiment, a portable ultrasound unit 100 has a gel pouch or pack and a gel feeding device that can be used to replenish the contact gel between the transducer surface and the skin.

Figure 3A:
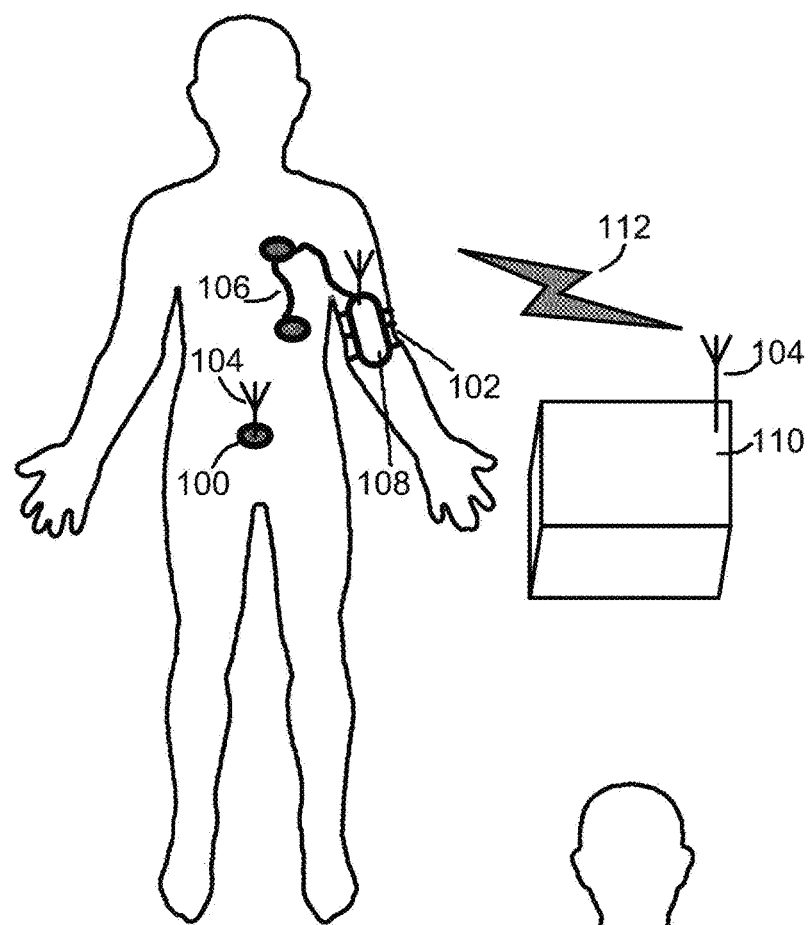
FIG. 3A illustrates a possible arrangement of portable ultrasound imaging units, interface unit and a remote patient monitoring system linked by a wireless data transmission link of a diagnostic ultrasound monitoring system according to one embodiment of the present invention.

In the preferred embodiment, a single or a multitude of portable ultrasound units 100 are connected to the remote patient monitoring system 110 by a wireless data transmission link 112 as illustrated by FIG. 3A.

The remote patient monitoring system 110 can be a computer workstation, a specialized unit or as simple as a smartphone or a tablet.

In another embodiment the remote patient monitoring system 110 can be a specially constructed miniature controller that can use a common flat TV to display ultrasound images and physiological information.

In another embodiment the remote patient monitoring system 110 can include a workstation with telemedicine capabilities relating diagnostic information to the remote observer and allowing the remote operator to control scanning process on the portable ultrasound unit 100.

In another embodiment, the portable ultrasound units 100, instead of connecting directly to the remote station 110, can be connected to an interface unit 108 secured to the patient by straps 102 that takes the task of communicating to the remote patient monitoring system by a wireless data transmission link 112.

In another embodiment, the interface unit 108 can be connected to ultrasound units 100 via wired link 106.

In another embodiment, the interface unit 108 can communicate to multitude of ultrasound units 100, combine their signals for transmission to the remote station 110.

In another embodiment, ultrasound units 100 that are connected to interface unit 108 by wired link can be supplied with power from the interface unit 108.

Figure 3B:
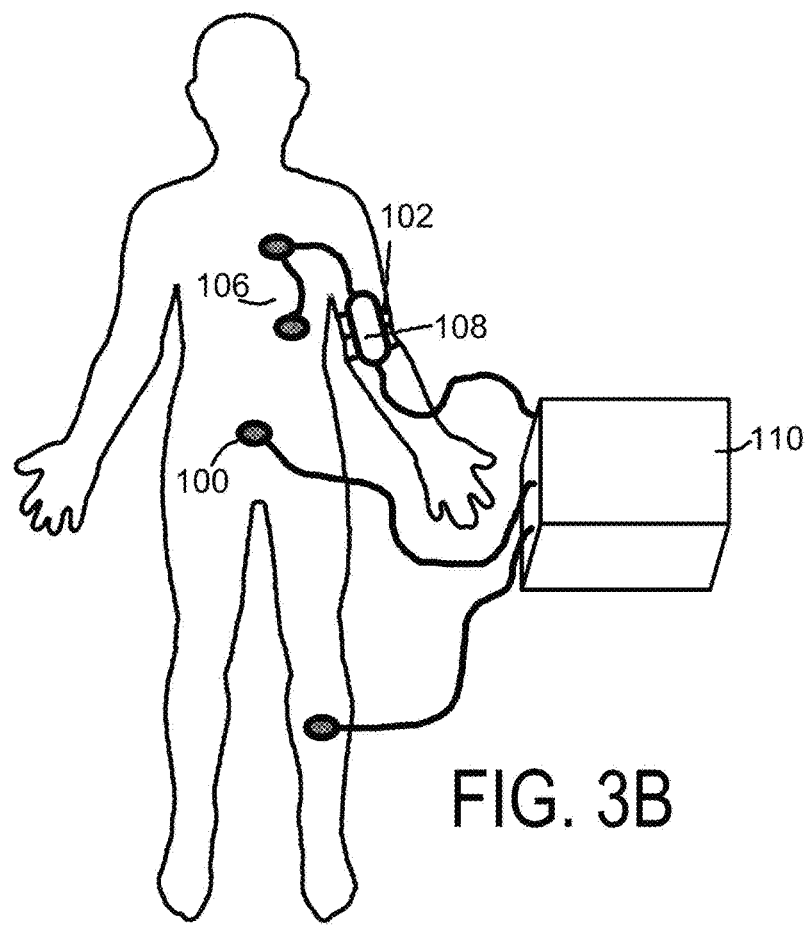
FIG. 3B illustrates a possible arrangement of portable ultrasound imaging units, interface unit and a remote patient monitoring system linked by a wired data transmission link of a diagnostic ultrasound monitoring system according to one embodiment of the present invention.

In another embodiment, illustrated by the FIG. 3B, some ultrasound units 100 could connect to remote station 110 by wired link directly or via interface unit 108.

Figure 3C:
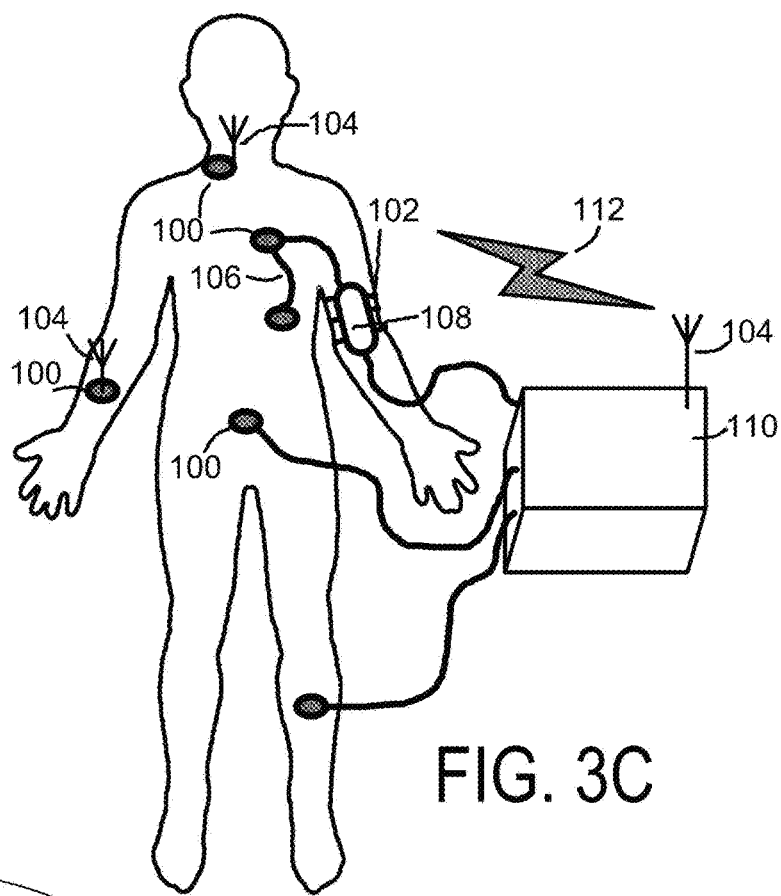
FIG. 3C illustrates a possible arrangement of portable ultrasound imaging units, interface unit and a remote patient monitoring system linked by a mixed wired/wireless data transmission link of a diagnostic ultrasound monitoring system according to one embodiment of the present invention.

In another embodiment, illustrated by the FIG. 3C, some ultrasound units 100 could connect to remote station 110 by wired link directly or via interface unit 108 while other ultrasound unit wirelessly.

One significant area for applications of portable ultrasound monitors is the cardiopulmonary resuscitation (CPR) procedures with the main goal of the portable ultrasound monitor being to provide the rescuer with information relating to the efficacy of chest compressions, return of spontaneous circulation, and underlying cardiac rhythm without cessation of external cardiac compression by the rescuer.

Currently during CPR, there is no method to detect return of spontaneous circulation without doing a physical "pulse check". A pulse check consists of stopping external cardiac compression (CPR) in order to palpate the carotid artery for a pulse. However, palpation is limited in accuracy and is unreliable (CPR is given when not needed 36% of the time and not given when needed 14% of the time according to Tibballs J., et al. "*Reliability of pulse palpation by healthcare personnel to diagnose pediatric cardiac arrest*". Resuscitation. 2009; 80). Further, current Advanced cardiac life support (ACLS) recommendations that any stoppage in CPR be limited as much as possible as delays in CPR decrease survival. The American Heart Association (AHA) and European Resuscitation Council developed the most recent ACLS guidelines. Certainly, not giving CPR when there is no cardiac output is detrimental to survival. However, giving CPR when the pulse has returned may also be detrimental as there may be initiation of an arrhythmia due to cardiac compression during certain portions of the heart's electrical cycle.

While ACLS CPR guidelines recommend a compression depth of 1.5 to 2 cm, with the goal of providing cerebral perfusion while there is inadequate cardiac contractility due to arrhythmia. Currently, there is no way to estimate if there is adequate cerebral blood flow except for palpation of the carotid artery during CPR. While a person palpating the carotid can provide feedback to the person performing CPR by asking for more depth of compression, this requires 2 people to perform the chest compressions, and this is not feasible in many settings where a cardiac arrest may occur (out of hospital settings, ambulance transport, wards or emergency departments in smaller hospitals).

ACLS recommendations also recommend "complete recoil" during compressions and specific compressions to respirations (compression to ventilation ratio). Both of these recommendations are related to allowing the heart of completely fill with blood prior to subsequent chest compressions. During a cardiac arrest event, carrying out these tasks can be difficult (tracking compression to ventilation and allowing for chest recoil). All of this can impact the cerebral blood flow. By having a blood flow monitor, the person performing CPR can be guided to the most effective rate, depth, and rhythm for effective CPR.

There is currently no method for detecting the underlying rhythm during CPR. During CPR, the chest where the electrocardiographic (ECG) monitors are located is subjected to movement. Consequently, the ECG signal reflects the motion of the chest and not the underlying cardiac electrical rhythm. Currently, CPR has to be stopped to evaluate the underlying rhythm. Since any stoppage in CPR results in a detriment in survival, current recommendations are that CPR should occur immediately after defibrillation and any stoppage in CPR should not occur more frequently than every 2 minutes. It is known that rapid defibrillation of ventricular fibrillation results in a higher success in return of spontaneous circulation. Thus being able to detect the underlying rhythm during CPR (without stopping CPR) could be an advantage for survival because there would be no need to stop CPR to check the rhythm and if ventricular fibrillation occurred during CPR, the provider would immediately know and could treat immediately.

Figure 4:
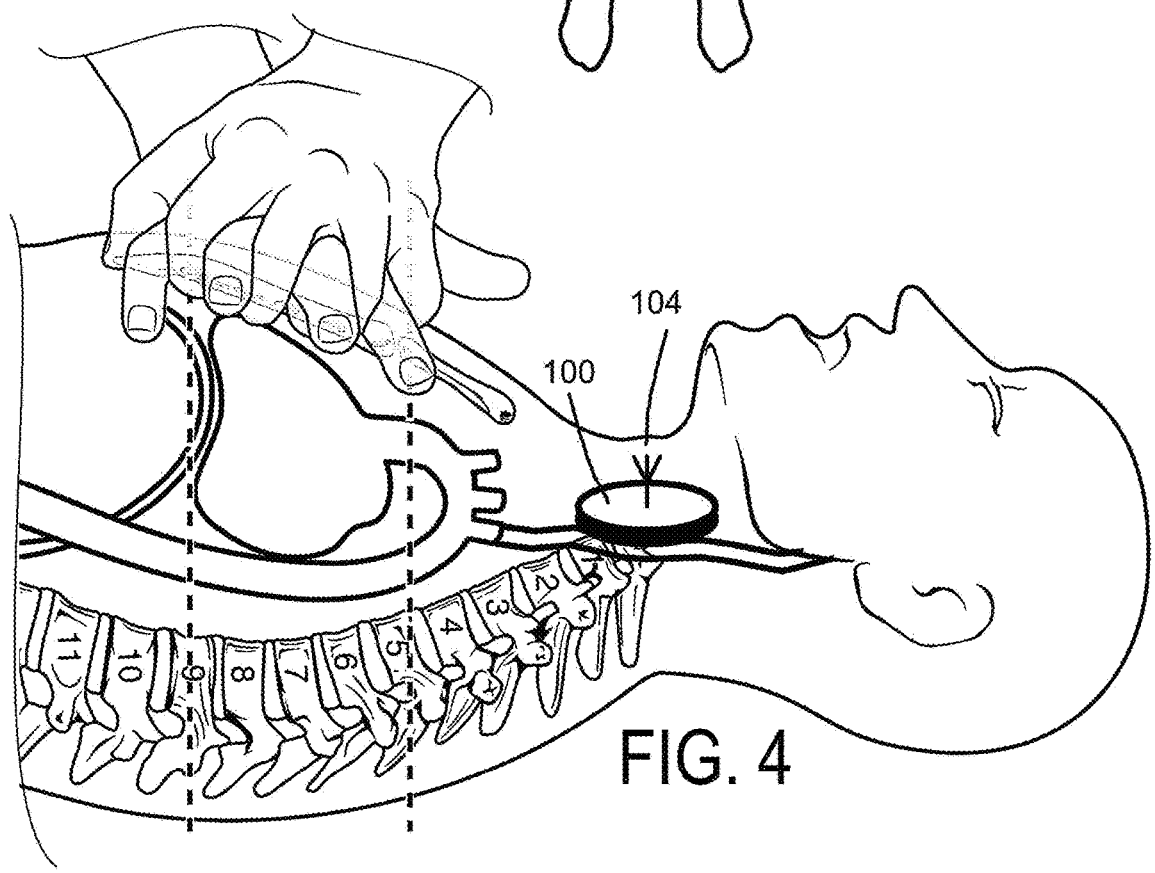
FIG. 4 illustrates a possible arrangement of portable ultrasound imaging unit of a diagnostic ultrasound monitoring system according to one embodiment of the present invention to monitor the coronary blood flow in course of administration of cardiopulmonary resuscitation (CPR).

FIG. 4 shows an example of application of current invention to the CPR procedure where portable ultrasound unit 100 is placed to measure the carotid blood flow. Again the unit 100 may be part of an analog store digital read beamforming system and method wherein each channel to use less than 40 milliwatts in operation and generally less than 25 milliwatts in operation.

Such tasks however can be accomplished with an aid of much simpler device, that have reduced number of sensors, but having an integrated visual display to guide the operator (rescuer) in course of CPR or to give an instant rating or gauging of patient health state. This may represent another embodiment of the same basic invention.

Figure 5:
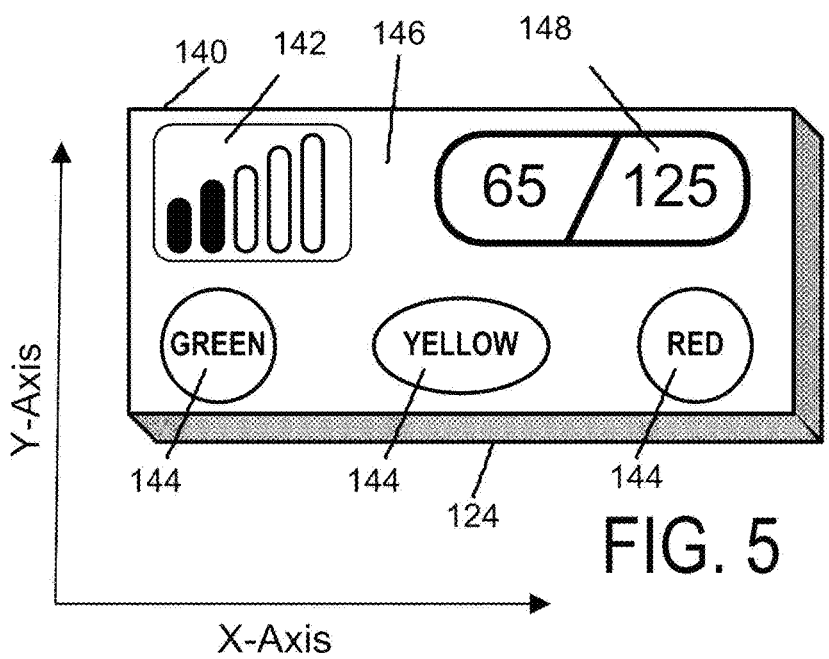
FIG. 5 illustrates another possible arrangement of functional blocks in a portable ultrasound imaging unit of a diagnostic ultrasound monitoring system according to one embodiment of the present invention.
Figure 6:
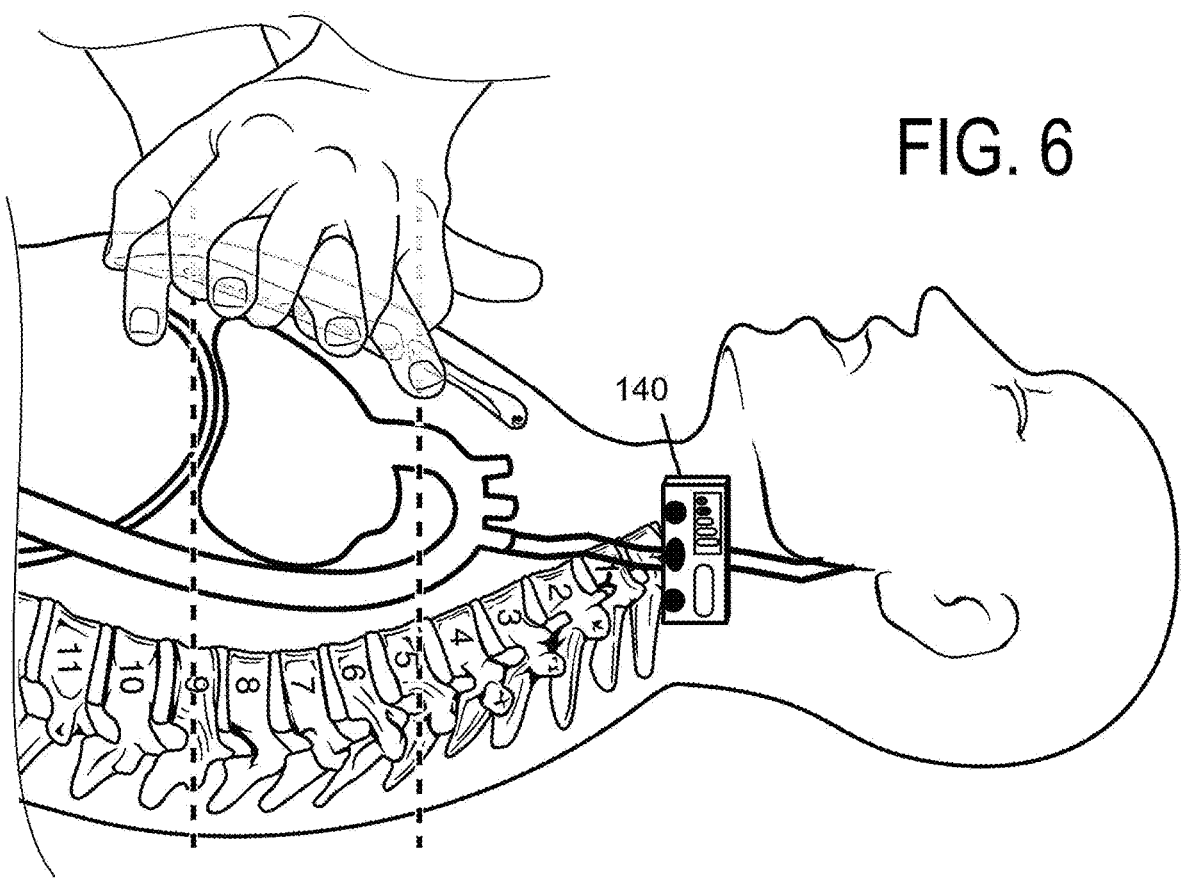
FIG. 6 illustrates a another possible arrangement of portable ultrasound imaging unit of a diagnostic ultrasound monitoring system according to one embodiment of the present invention to monitor the coronary blood flow in course of administration of cardiopulmonary resuscitation (CPR).

FIG. 5 shows a schematic outline of such a device 140 that consist of ultrasound arrays 124 capable of transmitting and receiving ultrasound signals for B mode and Doppler imaging at the bottom of the device and an integrated visual display 146 on the top surface of the device that schematically represent some vital data in real time via bar graph display 142, set of color indicator (i.e. green-yellow-red) 144 or a digital display 148, any combination of above listed displays with any other ways to display symbolic information or graphics.

An integrated adherent strap that facilitate the contact of the arrays 124 to the skin of the patient can be fixed to underside of the device 140 to hold device in place as well as to provide the acoustic contact for the array and ancillary sensors.

The strap could be a self-adherent strap (e.g., peel off cover revealing adhesive layer) or it could be an elastic band as it was described elsewhere in the patent.

The sensor could be incorporated into the wiring of the defibrillator pads of an AED (automatic external defibrillator) or as part of a Life Pak monitor defibrillator.

The ancillary sensor array could include a strain sensor for carotid blood flow, ECG sensors, and a CPR sensor (magnet). There would be a processor to correlate the CPR sensor signals to the strain (carotid) sensor and the ECG sensors.

The strain (carotid) sensor will be compared to the CPR (magnet) sensors to determine the effectiveness of the chest compressions. The processor using the strain sensor input and the CPR sensor input would give visual and auditory cues via display 146 to change the rate, rhythm, and force of the chest compressions to optimize the cerebral blood flow.

The ECG sensors would be correlated to the strain (carotid) sensor for detection of return of normal circulation. (ECG and Pulse correlated after removing the CPR signals).

The ECG sensor would be correlated to the CPR signal and with the CPR motion removed from the signal, the underlying rhythm can be determined in a real time basis during CPR. This information can be used to optimize defibrillation timing.

During periods of arrhythmia needing pacing, the ECG sensors can be used in conjunction with the strain (carotid) sensor to optimize the current output and sensitivity settings of the electrical paced rhythm for external pacing.

In one embodiment, multiple units 100 can be strapped to a patient, or on many different patients, and one or all monitors can be communicating with the remote station. The remote station 110 can be monitoring many separate patients and ultrasound units 100 simultaneously.

In one embodiment, intelligent software can be utilizing intelligent algorithms to process the ultrasound images and detect problems, issues or specific occurrences with the patient. During the long term monitoring (i.e. cardiac) the image acquisition can be triggered by an external event (i.e. change in pulse or blood pressure). If such issues are detected, alerts can be sounded for hospital staff, and emails, texts, etc. sent to alert the staff.

The remote station 110 can be programmed to scan wakeup, scan and produce ultrasound images or volumes, collect physiological information from a chosen patients and selected units 100, send them back to the remote station 100 or send them via email, text, etc. to appropriate medical personnel.

The portable ultrasound units 100 can be turned on, off and imaging parameters changed from the anywhere in the connected network. They can be programmed to scan for X period of time while recording video, and then do that every hour etc.

In the preferred embodiment, the array of ultrasound unit 100 is capable of obtaining 2D image slice in any projection or 3D volume with orientation and scan parameters remotely controlled by an operator.

In the preferred embodiment, portable ultrasound units 100 are capable of acquiring Doppler imaging.

In one embodiment, portable ultrasound units 100 can be capable BW ultrasound only.

In another embodiment, some portable ultrasound units 100 can be capable BW ultrasound only while other units are Doppler enabled.

In the preferred embodiment, data from few ultrasound imaging units 100 can be combined (fused) to create a single image or data volume. For example if one unit 100 images the heart from apical prospective while second unit looks at the heart parasternal, the data volumes could be fused to create a single cardiac image.

In another preferred embodiment, ultrasound units 100 could be equipped with position and orientation sensors such as inertial navigation system, such that the position and orientation of each unit 100 can be obtained and ultrasound data from such units could be combined into a single image or volume. Essentially, the multitude of position tracked units 100 can be seen as a single composite ultrasound array.

In another embodiment, one of such position tracked enabled units 100 can be used as a stationary imaging unit while another position tracked unit 100 is used for free hand image acquisition with data from all units fused for imaging and analysis.

It should be noted that the patient monitoring system is implemented partially in hardware, partially in firmware and partially in software such that precise boundaries between these parts can be established by the needs of the implementation. Further, in all descriptions and schematic diagrams the placement of elements or blocks, etc. that are secondary to the understanding of the invention are not strictly followed, assuming that anybody with ordinary knowledge of electronic design would understand their functions would determine where they should be placed in the actual working schematics, their structure, and parameters.

The above description describes an ultrasound patient monitoring system and method for an ultrasound imaging system comprising the steps of: i) Providing an ultrasonic array formed of individual ultrasonic array elements configured for transmission and receiving; ii) Dividing the individual array elements into individual channels, wherein each channel comprises at least one array element; iii) Creating a receiving input signal for each channel from inputs received from each array element of the channel; iv) Sampling each receiving input signal for each channel at a sampling rate and storing the sampled data in a data bank which is associated with that channel; v) Selecting at least one data from at least one channel for each particular output time for each beamforming instance in accordance with a beamforming algorithm; vi) Summing all of the selected data from the associated channels for the beamforming instance forming an analog beamformed received signal sample for the beamforming instance; vii) Digitizing the analog beamformed received signal sample; viii) Producing an image frame or a volume slice from the data; ix) Sending data to the remote workstation; and x) Sending physiological sensor information to the remote workstation.

Another advantage of the invention is that such compact system allows sending data and diagnostic images wirelessly to any image display equipped to receive such transmissions or having such a receiver attached to data ports such as USB or FireWire of the display unit.

Another advantage of the invention is that it has scalable architecture enabling the construction of distributed ultrasound arrays with any number of elements by linear expansion.

Another advantage of the invention is that it improves image quality and reduces the cost of systems built with 1.5D, 1.75D and 2D arrays.

Although the present invention has been described with particularity herein, the scope of the present invention is not limited to the specific embodiments disclosed. It will be apparent to those of ordinary skill in the art that various modifications may be made to the present invention without departing from the spirit and scope thereof.

What is claimed is:

1. A patient monitoring system for cardiopulmonary resuscitation (CPR) comprising:
 a standalone portable unit configured to be fixed to a stable position against the skin on a patient's body and configured to measure a carotid blood flow for detecting an underlying rhythm during cardiopulmonary resuscitation (CPR); and
 a display connected to the standalone portable unit configured to provide a rescuer with information including at least one of i) an efficacy of chest compressions, ii) a return of spontaneous circulation, and iii) an underlying cardiac rhythm without cessation of external cardiac compression by the rescuer, wherein the standalone portable unit includes an ultrasound imaging unit configured to be fixed to a stable position against the neck of a patient's body and capable of prolonged ultrasound data acquisition, including an ultrasound imaging array, transmit-receive circuitry, a beamformer, backend signal and image processing subsystem, power and communication subsystems.

2. The patient monitoring system for cardiopulmonary resuscitation (CPR) according to the claim 1 wherein the standalone portable unit is part of an analog store digital read beamforming system wherein each channel uses less than 40 milliwatts in operation.

3. The patient monitoring system for cardiopulmonary resuscitation (CPR) according to the claim 1 wherein the standalone portable unit is part of an analog store digital read beamforming system wherein each channel uses less than 25 milliwatts in operation.

4. The patient monitoring system for cardiopulmonary resuscitation (CPR) according to the claim 1 wherein the display connected to the standalone portable unit is configured to provide a rescuer with information including a return of spontaneous circulation.

5. The patient monitoring system for cardiopulmonary resuscitation (CPR) according to the claim 1 wherein the display connected to the standalone portable unit is configured to provide a rescuer with information including an efficacy of chest compressions.

6. The patient monitoring system for cardiopulmonary resuscitation (CPR) according to the claim 1 wherein the display connected to the standalone portable unit is configured to provide a rescuer with information including an underlying cardiac rhythm without cessation of external cardiac compression by the rescuer.

* * * * *